(12) United States Patent  (10) Patent No.: US 9,170,217 B2
Chapman  (45) Date of Patent: Oct. 27, 2015

(54) FACILITY AND METHOD FOR MOLECULAR STRUCTURE DETERMINATION

(71) Applicant: Deutsches Elektronen-Synchrotron DESY, Hamburg (DE)

(72) Inventor: Henry N. Chapman, Hamburg (DE)

(73) Assignee: Deutsches Elektronen-Synchrotron DESY, Hamburg (DE)

( * ) Notice: Subject to any disclaimer, the term of this patent is extended or adjusted under 35 U.S.C. 154(b) by 194 days.

(21) Appl. No.: 13/654,549

(22) Filed: Oct. 18, 2012

(65) Prior Publication Data

US 2013/0101086 A1    Apr. 25, 2013

(30) Foreign Application Priority Data

Oct. 19, 2011 (EP) .................................. 11185746

(51) Int. Cl.
*G01N 23/20* (2006.01)

(52) U.S. Cl.
CPC .... *G01N 23/20008* (2013.01); *G01N 2223/053* (2013.01); *G01N 2223/056* (2013.01); *G01N 2223/30* (2013.01)

(58) Field of Classification Search
USPC ...................................................... 378/53, 71
See application file for complete search history.

(56) References Cited

U.S. PATENT DOCUMENTS

| 6,409,832 | B2 * | 6/2002 | Weigl et al. ..................... 117/206 |
| 6,440,662 | B1 * | 8/2002 | Gerwen et al. ............... 435/6.11 |
| 7,303,727 | B1 * | 12/2007 | Dubrow et al. ............... 422/503 |
| 7,476,363 | B2 * | 1/2009 | Unger et al. .................. 422/504 |
| 7,746,980 | B1 * | 6/2010 | Schipper et al. ............... 378/79 |
| 2006/0262317 | A1 * | 11/2006 | Doak et al. ..................... 356/451 |
| 2011/0110566 | A1 * | 5/2011 | Sachs et al. ................... 382/128 |

FOREIGN PATENT DOCUMENTS

EP    1837642 A2    9/2007

OTHER PUBLICATIONS

Henry N. Chapman et al: "Femtosecond X-ray Protein Nanocrystallography", NATURE, vol. 470, No. 7332, Feb. 3, 2011, pp. 73-77; ISSN: 0028-0836, DOI: 10.1038/nature09750.

(Continued)

*Primary Examiner* — Phillip A Johnston
*Assistant Examiner* — Hsien Tsai
(74) *Attorney, Agent, or Firm* — Harness, Dickey & Pierce, P.L.C.

(57) ABSTRACT

A molecular structure determination facility includes a first X-ray source capable of emitting a pulsed coherent X-ray beam along a first emission direction and a plurality of first measurement stations aligned along the first emission direction. Each of the first measurement stations comprises a sample injector device for injecting a sample beam of a liquid into an interaction region, a focusing unit for focusing an X-ray beam, and a detector arranged around and comprising a central opening aligned with the emission direction, and being sensitive to X-rays emerging from the interaction region. A method uses the facility by emitting a coherent X-ray beam pulse using the first X-ray source, triggering the injector devices to inject sample beams of liquid into the interaction regions such that the coherent X-ray pulse intersects the sample beams of liquid in the interaction regions, and detecting X-rays emerging from the interaction regions using the detectors.

25 Claims, 3 Drawing Sheets

(56) References Cited

OTHER PUBLICATIONS

M. Marvin Seibert et al: "Single Mimivirus Particles Intercepted and Imaged With an X-ray Laser", NATURE, vol. 470, No. 7332, Feb. 3, 2011, pp. 78-81, ISSN: 0028-0836, DOI: 10.1038/nature09748.

L. Strüder et al.: "Large-Format, High-Speed, X-Ray pnCCDs Combined With Electron and Ion Imaging Spectrometers in a Multipurpose Chamber for Experiments at 4th Generation Light Sources", Nuclear Instruments and Methods in Physics Research A, vol. 614, Jan. 4, 2010, pp. 483-496.

P. Fromme et al.: "Femtosecond Nanocrystallography Using X-Ray Lasers for Membrane Protein Structure Determination", Current Opinion in Structural Biology, vol. 21, No. 4, Jan. 1, 2011, pp. 509-516, ISSN: 0959-440X.

Robert Hartmann et al.: "Large Format pnCCDs as Imaging Detectors for X-Ray FreeElectron-Lasers", Nuclear Science Symposium Conference Record, 2008. NSS '08. IEEE (Oct. 19-25, 2008), IEEE, Piscataway, NJ, USA, Oct. 19, 2008, pp. 2590-2595, ISBN: 978-1-4244-2714-7.

E.M.H. Duke et al.: "Macromolecular Crystallography at Synchrotron Radiation Sources: Current Status and Future Developments", Proceedings—Royal Society. Mathematical, Physical and Engineering Sciences, vol. 466, No. 2124, Jan. 1, 2010, pp. 3421-3452, ISSN: 1364-5021.

\* cited by examiner

FACILITY AND METHOD FOR MOLECULAR STRUCTURE DETERMINATION

CROSS-REFERENCE TO RELATED APPLICATIONS

This application claims the benefit and priority of European Patent Application Number EP 11185746.2, which was filed on Oct. 19, 2011. The disclosure of the above application is incorporated herein by reference in its entirety.

FIELD

The invention relates to a facility and a method for molecular structure determination using coherent X-rays.

BACKGROUND

The structure of biological macromolecules is primarily detected using X-ray crystallography where the diffraction patterns of coherent X-rays interacting with crystallized biological macromolecules is recorded. To obtain highly resolved representations of the molecule's structure these diffraction patterns have to be recorded at wide angles where diffraction intensities are very low. The diffraction intensity is proportional to the number of diffracted X-rays and the number of unit cells in the illuminated single crystal. Therefore, in order to get sufficient diffraction intensities large crystals have to be irradiated with large numbers of photons.

The number of diffracted photons can easily be increased by extending the irradiation time. Unfortunately, many crystals only tolerate dose up to 30 MGy ($3\times10^7$ J/kg) before substantial structural damages occur that destroy the crystalline structure. The dose required to obtain sufficient diffracted intensities can be reduced by growing larger crystals with more unit cells. For large macromolecules such as proteins and protein complexes staying below the tolerable dose requires crystals of many hundreds of micrometers in size. Growing crystals of this size and high quality is a very difficult and time consuming trial-and-error process that is currently the major bottleneck of X-ray crystallography. Even more challenging are membrane-bound proteins that are critical for drug design but notoriously difficult to crystallize.

The crystallization bottleneck can be overcome by using serial femtosecond crystallography. Here, nanocrystals are not irradiated with conventional synchrotron radiation but a collection of nanocrystals are irradiated one at a time with ultra-short coherent X-ray pulses. This method bears several advantages as the nanocrystals can be more easily grown and substantially higher doses can be employed.

Nanocrystals of many macromolecules can be grown by driving a protein suspension into supersaturation. If the proteins in the supersaturated suspension are quickly precipitated many small nanocrystals are formed around many nucleation sites.

The ultra-short coherent X-ray pulses are commonly generated with X-ray free electron lasers (X-ray FELs) and have a pulse length of approximately 100 fs (10-13 s). If the X-ray FEL pulse is focused to micrometer dimensions it can deposit doses in a crystal that exceed those conventionally tolerated by several magnitudes. As expected, the high dose of the X-ray pulse completely vaporizes the nanocrystal but only after the pulse has passed through it. The short pulse "outruns" the radiation damage as the inertia of the atoms in the crystal is sufficiently large to keep their movements within tolerable bounds during the time that the beam passes through the crystal. Hence, the diffraction pattern that is recorded on the detector corresponds to the undamaged crystal structure.

A single pulse does of course only give a diffraction pattern of the crystal structure in one particular orientation. In order to reconstruct the full three-dimensional structure of the molecule diffraction patterns obtained under many orientations have to be combined. Unlike conventional powder diffraction crystallography the data from many crystals is not summed up without regard to their orientation. Instead each diffraction pattern is indexed i.e. the observed peak intensities are labeled according to their origin in the lattice of the crystal. Those peaks that carry the same index are then summed up. The summation therefore averages over crystal shapes, crystal sizes and crystal orientation. Due to their small size the crystals are coherently illuminated which, combined with the index summation, leads to brighter intensities than those obtained with conventional crystallography on large crystals. It is therefore expected that more information can be extracted. It may, for example, be possible to extract a three dimensional vector gradient of the intensities which would increase the measured information by a factor of four. This would allow the use of novel phasing methods to obtain the molecular structure of the macromolecule.

In total, diffraction patterns from more than 10,000 crystals have to be measured and summed up. In these experiments approximately 10% of the X-ray pulses hit a nanocrystal. Out of the recorded diffraction patterns roughly half can be indexed successfully. Therefore, a total of 200,000 X-ray pulses is required to obtain sufficient data for a complete reconstruction of the structure of the macromolecule. Current X-ray FELs achieve a repetition rate of 120 Hz i.e. for each macromolecule at least 28 minutes of beam time is required.

SUMMARY

In the view of the foregoing discussion it is therefore the object of the present invention to provide a facility and a method for molecular structure determination that reduces the time that is required to determine the structure of a single molecule significantly and thereby drastically increases the throughput of molecules that can be studied using a single X-ray FEL.

According to a first aspect of the present invention a molecular structure determination facility comprises a first X-ray source capable of emitting a pulsed coherent X-ray beam along a first emission direction, a plurality of first measurement stations aligned consecutively along the first emission direction, wherein each of said first measurement stations comprises a sample injector device for injecting a sample beam of liquid into an interaction region located on said first emission direction, a focusing unit for focusing an X-ray beam in a focal spot located in said interaction region and a detector being sensitive to X-rays emerging from said interaction region, said detector being arranged around said first emission direction and on that side of said interaction region facing away from said X-ray source, wherein said detector comprises a central opening aligned with said emission direction.

Thus, the present invention provides a solution for the above problem by providing a molecular structure determination facility comprising a first X-ray source capable of emitting a pulsed coherent X-ray beam along a first emission direction. This X-ray source may be but is not limited to an undulator employed in an X-ray Free Electron Laser (X-ray FEL).

Along the first emission direction a plurality of first measurement stations is consecutively aligned so that the X-ray beam may pass through the stations. Each of said first measurement stations comprises a sample injector device for injecting a sample beam of a liquid into an interaction region located on said first emission direction. The injector device may, for example, provide a gas-focused aerosol jet of a suspension carrying the nanocrystals, a continuous liquid water stream carrying the nanocrystals or a pulsed stream of liquid carrying the nanocrystals. A pulsed stream of liquid may, for example, be injected at the same rate as the X-ray pulses arriving at the measurement station. Thereby, the consumption of the sample suspension is reduced, since less material will be flowing overall, yet the material will be flowing during the time that X-ray pulses intersect the interaction region. This embodiment is especially advantageous when the sample suspension can only be obtained in limited volumes.

Said liquid may, for example, be a suspension of nanocrystals in liquid, a solution of uncrystallized protein macromolecules or other biological objects such as complexes. Uncrystallized protein macromolecules will give rise to less information regarding the scattering pattern but could be useful in time-resolved experiments where the initial structure is well known. It would be possible, for example, to determine the change of structure under illumination with a visible or an IR laser or after mixing of two proteins.

Said first measurement stations further comprise a focusing unit for focusing an X-ray beam in a focal spot located in said interaction region. The X-ray beam could, for example, be focused using a compound refractive lens or grazing-incidence curved-mirror optics such as Kirkpatrick-Baez mirrors.

Additionally, said first measurement stations comprise a detector being sensitive to X-rays emerging from said interaction region. Said detector is arranged around said first emission direction and on that side of said interaction region facing away from said X-ray source. Said detector comprises a central opening aligned with said emission direction. Advantageously, said detector comprises a set of two low-noise, X-ray p-n junction charge-coupled device (pnCCD) modules or high-repetition rate pixel-array detectors.

The present invention provides a possible way of increasing the throughput of molecular structure determination facility without requiring multiple pulsed X-ray sources.

The invention essentially proceeds from the fact that less than 1% of the incident X-ray beam pulse's energy is absorbed when the beam interacts for the first time with a sample. More than 99% of the incident X-ray beam pulse's energy is transmitted undiffracted through the sample and passes through said central opening in said detector. Thereby, the detector is spared from severe damage by the X-ray beam and the X-ray beam can be utilized for further diffraction measurements in said consecutively aligned measurement stations.

Upon entering the measurement station closest to the X-ray beam source the X-ray beam is focused to a focal spot within the interaction region of the first station. In this first focal spot a focal width of 0.1 to 0.5 micrometer could be achieved, for example. Subsequently, the beam is divergent once it has passed the focal spot. Upon entering the next consecutively aligned measurement station the beam is refocused to a focal spot within the interaction region of said next consecutively aligned measurement station. By way of example a focal width of 1 micrometer could be achieved. Consequently, the beam has to be refocused again in subsequent measurement stations where, for example, a focal width of 2 to 3 micrometers could be expected. The intensity of the X-ray beam decreases with increasing spot size and therefore measurement stations nearer to the X-ray source have higher X-ray beam intensities.

By way of example, all measurement stations can be used to analyze the same macromolecule which reduces the time required to obtain sufficient data for a full 3D reconstruction by a factor equal to the number of measurement stations. In this case any of the injector devices are supplied with the same macromolecule suspension.

By another way of example, nanocrystals from different macromolecules can be screened at each measurement station. The measurement station closest to the X-ray beam source provides the smallest focal width and hence highest intensity of the X-ray beam. It may, for example, be used to obtain diffraction data for very small nanocrystals or provide diffraction data to reconstruct highly resolved structures. However, the high intensities of the measurement station nearest to the X-ray beam source may not be required for all nanocrystals. These nanocrystals could as well be studied with sufficient resolution at the other measurement stations.

In another exemplary fashion, any sample suspension of nanocrystals could first be analyzed in the measurement station with the lowest X-ray beam intensity. If the intensities of the recorded diffraction patterns turn out to be too weak the sample is analysed at another measurement station with a higher X-ray beam intensity.

Alternatively, one or more of the measurement stations with lower X-ray beam intensities could be used for screening measurements to determine whether nanocrystals diffract at all. Nanocrystal suspensions from a range of preparation conditions can be tested in series to determine which preparation condition gives the highest diffraction intensities. The selected suspension can then be used in a measurement station with a higher intensity for structure determination measurements.

In a preferred embodiment, a first X-ray beam analysing device is located on said first emission direction on that side of said first measurement stations facing away from said first X-ray source. Said first X-ray beam analysing device may be used to optimize X-ray beam characteristics. The focusing of the X-ray beam by said focusing units comprised in said first measurement stations or the position of the first emission direction relative to the sample beams of liquid can be monitored by the first X-ray beam analysing device, for example.

It is particularly advantageous for the facility to comprise a second X-ray source for emitting a pulsed coherent X-ray beam along a second emission direction. Along said second emission direction a plurality of second measurement stations is consecutively aligned. Each of said second measurement stations comprises a sample injector device for injecting a sample beam of a liquid into an interaction region located on said second emission direction, a focusing unit for focusing an X-ray beam in a focal spot located in said interaction region and a detector being sensitive to X-rays emerging from said interaction region. The detector is arranged around said second emission direction on that side of said interaction region facing away from said second X-ray source. Said detector comprises a central opening aligned with said second emission direction.

A second X-ray source emitting along a second emission direction is especially advantageous as it further increases the number of suspension samples that can be studied in the facility. The sampling rate of a single emission direction is limited by the repetition rate of current X-ray FELs that is, for example, at 120 Hz. It is further limited by the read-out frequency of the detectors which is currently, for example, at 200 Hz and the rate with which the injector devices could supply a macromolecule suspension samples to the interaction region. Therefore, a second array of X-ray source and measurement stations would double the throughput of the molecular structure determination facility.

It is again preferred that a second X-ray beam analysing device is located on said second emission direction on that side of said second measurement stations facing away from said second X-ray source. Said second X-ray beam analysing device may be used to optimize X-ray beam characteristics. The focusing of the X-ray beam by said focusing units comprised in said second measurement stations or the position of the second emission direction relative to the sample beams of liquid can again be monitored.

In a preferred embodiment, a source of a pulsed electron beam is provided for supplying a pulsed electron beam to said first and second X-ray sources. Said source of said pulsed electronbeam may, for example, be a linear electron accelerator, an electron synchrotron or a combination of the two. Additionally, a switching magnet is provided having an input connection and first and second output connections. Said switching magnet is capable of diverting a pulsed electron beam entering the magnet via said input connection to either of said first and second output connections. Said input connection is connected with said source of a pulsed electron beam, said first output connection is connected with said first X-ray source and said second output connection is connected with said second X-ray source.

An advantage of the latter embodiment is the use of said single source of said electron beam to provide both X-ray sources with electrons. Electron sources that provide sufficiently high energies for X-ray FEL are very large and costly to build and maintain. Their power consumption is also considerably high. Undulators on the other hand are compared to the accelerator small and cheap. Novel accelerators may, for example, provide electron pulses with a repetition rate of up to 10 kHz. An increase of the read-out frequency of the detectors to 1 kHz from today's 200 Hz would allow for a single electron source to provide electrons for up to 10 lines of X-ray sources and measurement stations. Thereby, the throughput of the facility is considerably increased without requiring another electron source.

It is particularly advantageous for the facility to comprise a central sample preparation unit to which said injector devices are connected. Said central sample preparation unit comprises a reservoir system including a plurality of reservoirs, a plurality of pumps and a switching unit. Each of said reservoirs is connected with an input of one of said pumps. The switching unit has a plurality of inputs and a plurality of outputs, wherein the output of each of said pumps is connected with an input of said switching unit and said outputs of the switching unit are connected with the injector devices.

A sample preparation unit as described above could, for example, automatically carry out the different operation modes of the facility that have been described above. Additionally, the sample preparation could be connected to a feedback system that provides information about the diffraction patterns recorded in the measurement stations. Thereby, the flow rate of the sample suspensions or even the preparation of the sample suspensions could be controlled. The sample preparation system could also be used to automatically clean the injection devices with a neutral liquid in between two different sample suspensions.

In a preferred embodiment of the present invention one or a plurality of said measurement stations further comprises a second sample injector device for injecting a second sample beam of liquid into said interaction region. Two macromolecule suspensions could be simultaneously injected into the interaction region such that they mix. If these macromolecules are uncrystallized a reaction may be initiated which changes the structure of the molecules and also the diffraction patterns of the macromolecules. Thereby, a molecular structure determination facility of the preferred embodiment can be used to study the changes of molecular structures within a reaction. It is further possible, for example, to obtain diffraction patterns at different points in time after the beginning of the mixing of the sample beam of liquid and the other sample beam of liquid. Thereby, the structural changes of the molecules in the suspension due to the reaction can be monitored in a time-resolved fashion. It is also conceivable that a measurement station according to this preferred embodiment may be used in different assemblies than the present invention. In particular, the aforementioned independently inventive concept of a measurement station having a sample injector device and a second sample injector device could be used in a molecular structure determination facility comprising a sole measurement station.

In another preferred embodiment one or a plurality of said measurement stations further comprise a laser device emitting a laser beam intersecting said interaction region. The laser device could be emitting, for example, a visible or an infrared laser beam. Such a laser beam could be used to initiate a photo reaction in the macromolecules in the sample beam of liquid wherein the structure of the macromolecules in the suspension changes. Thereby, a molecular structure determination facility of the preferred embodiment can be used to study the changes of molecular structures within a photo reaction. It is further possible, for example, to obtain diffraction patterns at different points in time after the initiation of the photo reaction. Thereby, the structural changes of the molecule due to the photo reaction can be monitored in a time-resolved fashion. It is conceivable that a measurement station according to this preferred embodiment may be used in different assemblies than the present invention.

In a preferred embodiment, one or a plurality of said measurement stations further comprise a backscatter detector being sensitive to X-rays emerging from said interaction region, said backscatter detector being arranged around said first emission direction and on that side of said interaction region facing away from said detector, wherein said backscatter detector comprises a central opening aligned with said emission direction. A combination of the diffraction patterns detected by the detector and the backscatter detector is preferable as it allows reconstructing the structure of the molecules with a resolution of up to half the wavelength of the coherent X-ray beam. Advantageously, said backscatter detector comprises a set of two low-noise, X-ray p-n junction charge-coupled device (pnCCD) modules or high-repetition rate pixel-array detectors.

According to a second aspect of the present invention a method is provided that uses the above described facility and comprises the following steps of emitting a coherent X-ray beam pulse along said first emission direction using said first X-ray source, triggering said injector devices provided in said first measurement stations to inject sample beams of liquid into said interaction regions aligned along said first emission direction such that said coherent X-ray pulse intersects said sample beams of liquid in said interaction regions aligned along said first emission direction, and detecting X-rays emerging from said interaction regions using said detectors provided in said first measurement stations.

A preferred embodiment of the method additionally comprises the steps of emitting a coherent X-ray beam pulse along said second emission direction using said second X-ray source, triggering said injector devices comprised in said second measurement stations to inject sample beams of liquid into said interaction regions aligned along said second emission direction such that said coherent X-ray pulse intersects said sample beams of liquid in said interaction regions aligned along said second emission direction, and detecting X-rays emerging from said interaction regions using said detectors comprised in said second measurement stations.

In another preferred embodiment of the method according to the present invention the step of triggering said injector device to inject the sample beam of liquid into said interaction region further comprises triggering said second injector device to inject said second sample beam of liquid into said interaction region such that said sample beam of liquid and said second sample beam of liquid mix in said interaction region and such that said coherent X-ray beam pulse intersects said sample beam of liquid mixed with said second sample beam of liquid in said interaction region.

It is further preferred that said step of triggering said injector devices to inject the sample beam of liquid into said interaction region further comprises triggering said laser device to emit the laser beam, such that said laser beam intersects said sample beam of liquid in said interaction region comprised in said measurement station.

It is further preferred that said step of triggering said injector devices to inject the sample beam of liquid into said interaction region further comprises triggering said laser device to emit the laser beam, such that said laser beam intersects said sample beam of liquid mixed with said second sample beam of liquid in said interaction region comprised in said measurement station.

Said methods are advantageous for the same reasons that have already been stated above for the claimed molecular structure determination facility.

BRIEF DESCRIPTION OF THE DRAWINGS

A preferred embodiment of the present invention will now be described, by way of example only, with reference to the accompanying drawings of which.

DETAILED DESCRIPTION

Figure 1:
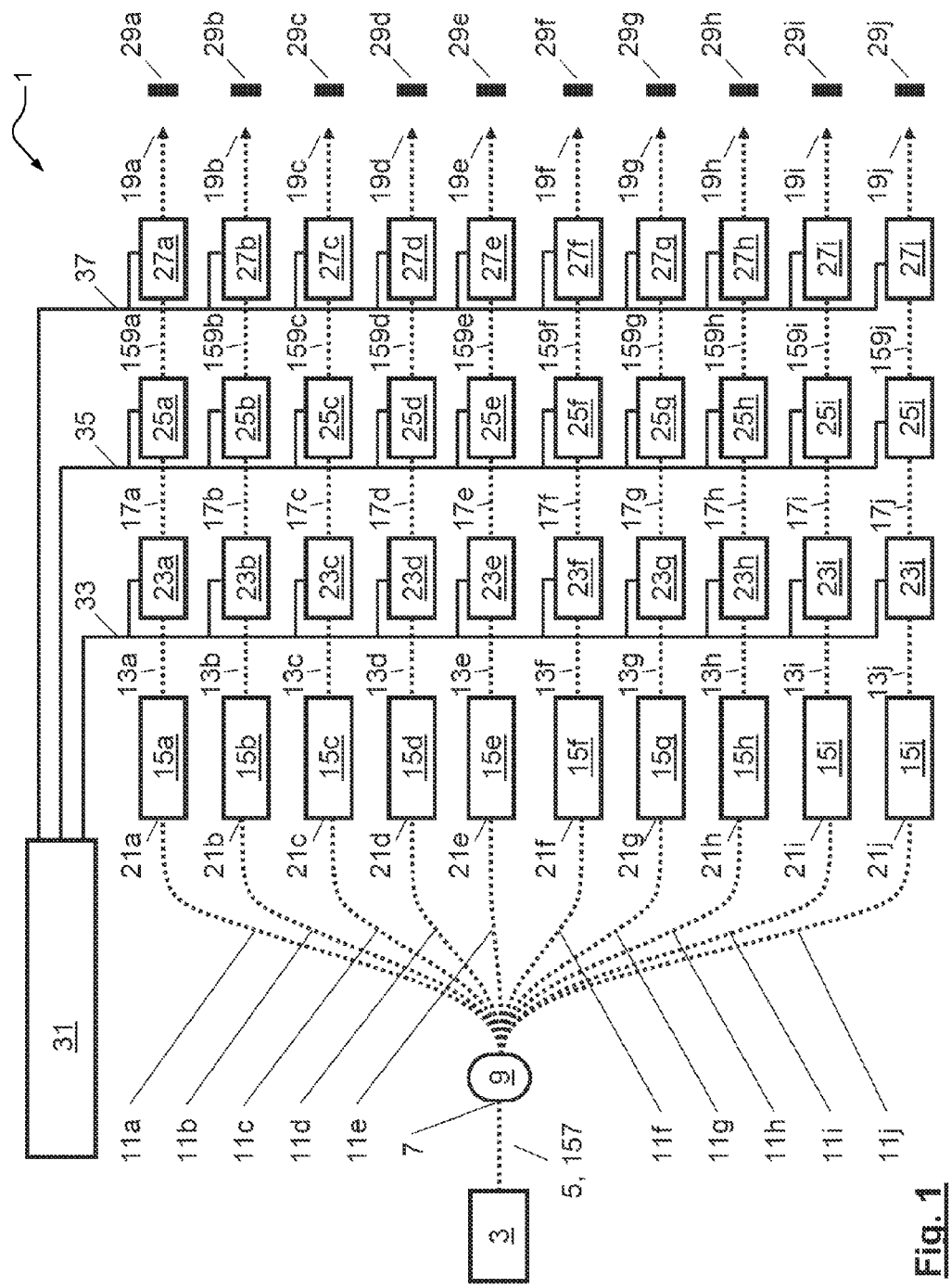
FIG. 1 is a schematic drawing of the general structure of an exemplary embodiment of a facility for molecular structure determination according to the present invention.

FIG. 1 shows the general structure of a preferred embodiment of a molecular structure determination facility 1 according to the present invention. A source 3 of a pulsed electron beam 5 is connected with an input connection 7 of a switching magnet 9. Said switching magnet 9 comprises in this preferred embodiment ten output connections 11a to 11j.

The molecular structure determination facility 1 further comprises ten measurement lines 13a to 13j. Moreover it is conceivable that the molecular determination facility 1 comprises more or less than ten measurement lines 13a to 13j.

Each measurement line 13a to 13j comprises an X-ray source 15a to 15j emitting a pulsed coherent X-ray beam 17a to 17j along a linear emission direction 19a to 19j. The input 21a to 21j of each X-ray source 15a to 15j is connected with an output connection 11a to 11j of the switching magnet 9.

In this preferred embodiment within each measurement line 13a to 13j three measurement stations 23a to 23j, 25a to 25j and 27a to 27j are aligned consecutively along the emission direction 19a to 19j but it is also within the scope of the present invention that each measurement line 13a to 13j comprises more or less than three measurement stations 23a to 23j, 25a to 25j and 27a to 27j.

An X-ray beam analysing device 29a to 29j is located on the emission direction 19a to 19j on that side of the measurement stations 23a to 23j, 25a to 25j and 27a to 27j that is facing away from the X-ray source 15a to 15j, i.e. at the end of each measurement line 13a to 13j remote from the X-ray source 15a to 15j. In a preferred embodiment the X-ray beam analysing device 29a to 29j comprises means for X-ray beam wavefront diagnostics.

The molecular structure determination facility 1 further comprises a schematically drawn sample preparation unit 31. Conduits 33, 35, 37 connect the sample preparation unit 31 with the measurement stations 23a to 23j, 25a to 25j and 27a to 27j. Conduits 33, 35, 37 comprise discrete conduits connecting each measurement station 23a to 23j, 25a to 25j and 27a to 27j independently with the sample preparation unit 31 such that each measurement station 23a to 23j, 25a to 25j and 27a to 27j can be supplied independently with macromolecule suspensions. Discrete conduits to each measurement station 23a to 23j, 25a to 25j and 27a to 27j have been omitted for the sake of clarity in FIG. 1 but are indicated in FIG. 2.

Figure 2:
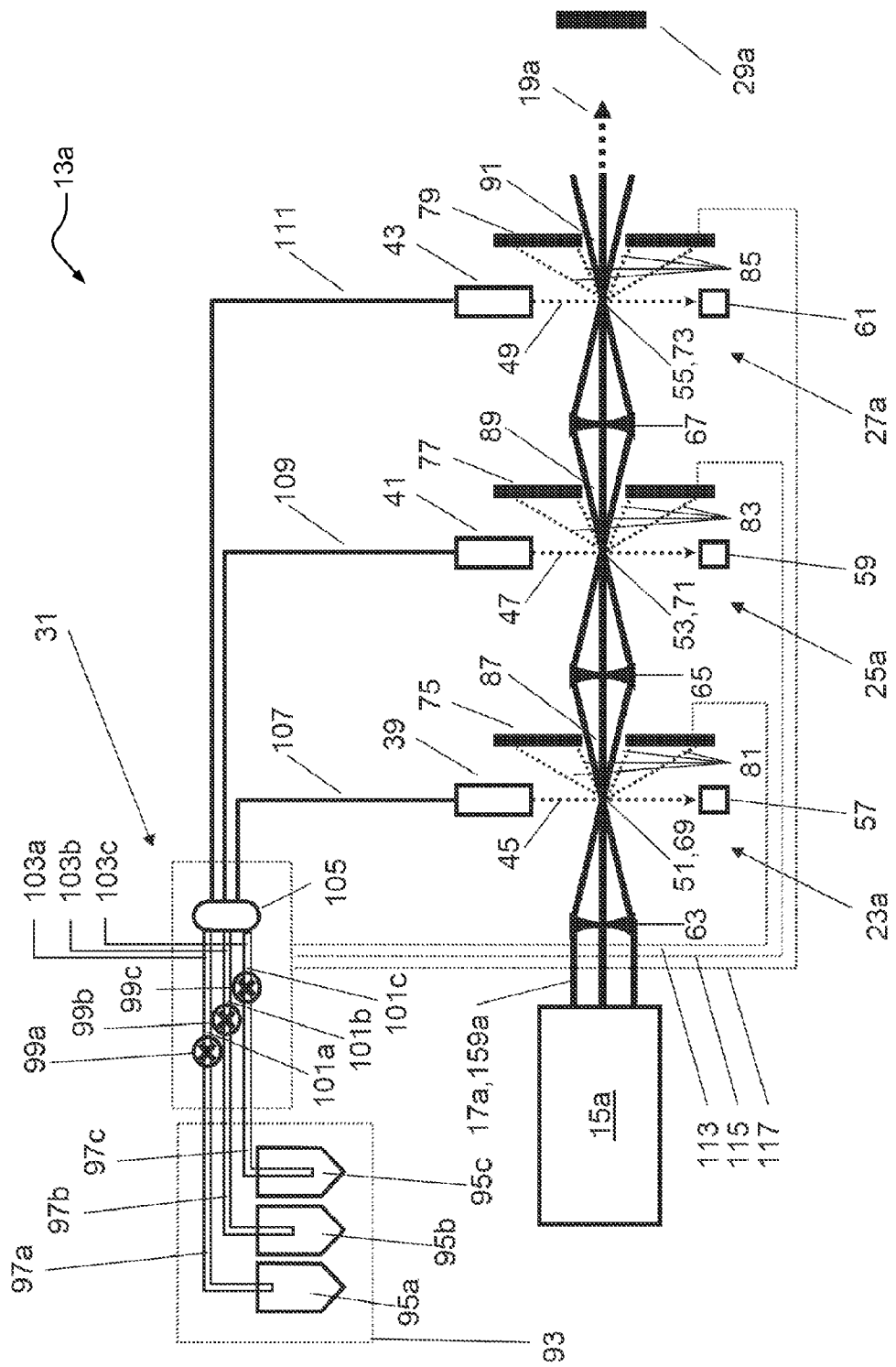
FIG. 2 is a partial schematic drawing of the embodiment of FIG. 1 showing three measurement stations aligned along the emission direction and the sample preparation system.

A detailed drawing of a measurement line 13a comprising three measurement stations 23a, 25a, 27a and the central sample preparation unit 31 is shown in FIG. 2. It is conceivable that FIG. 2 shows any of the measurement lines 13a to 13j. The measurement stations 23a, 25a, 27a are consecutively aligned on the emission direction 19a of the X-ray source 15a. Each measurement station 23a, 25a, 27a comprises a sample injector device 39, 41, 43 for injecting a sample beam of liquid 45, 47, 49 into an interaction region 51, 53, 55 located on the emission direction 19a. The sample beam of liquid is collected in sample beam dumps 57, 59, 61. In a preferred embodiment of the present invention the sample beam of liquid 45, 47, 49 collected in said sample beam dump 57, 59, 61 is recycled. Thereby, any crystals or molecules that have not been previously hit by an X-ray pulse can be re-injected either in the same or another measurement station 23a to 23j, 25a to 25j and 27a to 27j.

Each measurement station 23a, 25a, 27a further comprises a focusing unit 63, 65, 67 for focusing an X-ray beam 17a in a focal spot 69, 71, 73 located in said interaction region 51, 53, 55. Within each measurement station 23a, 25a, 27a a detector 75, 77, 79 that is sensitive to X-rays 81, 83, 85 emerging from said interaction region 51, 53, 55 is arranged around said emission direction 19a. The detector 75, 77, 79 is located on that side of the interaction region 51, 53, 55 facing away from the X-ray source 15a. Furthermore, the detector 75, 77, 79 comprises a central opening 87, 89, 91 aligned with the emission direction 19a.

The measurement line 13a further comprises an X-ray beam analysing device 29a located on the emission direction 19a on that side of the measurement stations 23a, 25a, 27a facing away from the X-ray source 15a.

Said sample preparation unit 31 comprises a reservoir system 93 including three reservoirs 95a to 95c. Each of the reservoirs 95a to 95c is connected with an input 97a to 97c of one of three pumps 99a to 99c. The outputs 101a to 101c of the pumps 99a to 99c are connected to the inputs 103a to 103c of a switching unit 105. The outputs 107, 109, 111 of the switching unit 105 are each connected with one of the sample injector devices 39, 41, 43 via separate conduits. The switching unit 109 comprises additional outputs each connected to one of the measurement stations 23b to 23j, 25b to 25j and 27b to 27*j*. For the sake of clarity these output are not shown in FIG. 2. It is also conceivable that the reservoir system 31 comprises more or less than three reservoirs 95*a* to 95*c* and pumps 99*a* to 99*c*.

Said measurement line 13*a* further comprises three feedback systems 113, 115, 117. Each feedback system 113, 115, 117 connects one of the detectors 75, 77, 79 with the sample preparation system 31.

Figure 3:
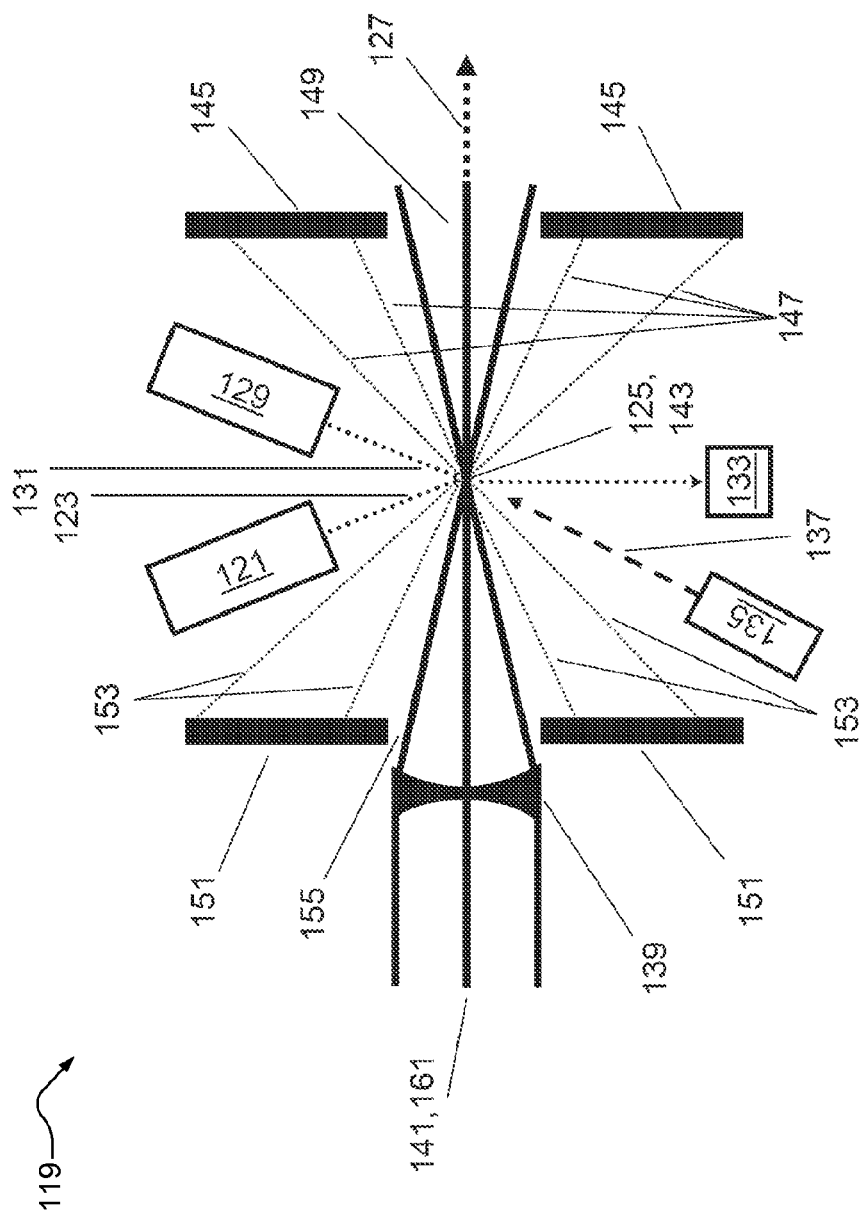
FIG. 3 is a schematic drawing of a second embodiment of a measurement station according to the present invention.

A second embodiment of a measurement station 119 according to the present invention is shown in FIG. 3. Even though this embodiment is described as being part of an assembly of a plurality of measurement stations 23*b* to 23*j*, 25*b* to 25*j* and 27*b* to 27*j* being aligned on an emission direction 19*a* to 19*j*, it is also possible that this independently inventive concept of a measurement station 119 is employed as a sole measurement station 119 in a molecular structure determination facility 1. Said measurement station 119 comprises a sample injector device 121 for injecting a sample beam of liquid 123 into an interaction region 125 located on the emission direction 127 of an X-ray source (not shown). It further comprises a second sample injector device 129 for injecting a second sample beam of liquid 131 into the interaction region 125. The sample beam injector 121 and the second sample beam injector 129 are connected to a central sample preparation unit 31. The sample preparation unit 31 and connections to the sample preparation unit 31 have been omitted in FIG. 3 for reasons of clarity. It is conceivable that the sample beams of liquid 123, 131 are injected by the sample injector devices 121, 129 simultaneously or one at a time. The sample beams of liquid 123, 131 are collected in a sample beam dump 133. In a preferred embodiment of the present invention the sample beams of liquid 123, 131 collected in said sample beam dump 133 are recycled.

The measurement station 119 further comprises a laser device 135 emitting a laser beam 137 that intersects the interaction region 125. In an exemplary fashion said laser device 135 may be emitting a laser beam 137 of visible light or infrared light.

Additionally, the measurement station 119 comprises a focusing unit 139 for focusing an X-ray beam 141 in a focal spot 143 located in said interaction region 125. Within the measurement station 119 a detector 145 that is sensitive to X-rays 147 emerging from said interaction region 125 is arranged around said emission direction 127. The detector 145 is located on that side of the interaction region 125 facing away from the X-ray source (not shown). Furthermore, the detector 145 comprises a central opening 149 aligned with the emission direction 127.

Furthermore, the measurement station 119 comprises a backscatter detector 151 that is sensitive to X-rays 153 emerging from said interaction region 125. The backscatter detector 151 is arranged around said emission direction 127 on that side of the interaction region 125 facing away from the detector 145. Additionally, the backscatter detector 151 comprises a central opening 155 aligned with the emission direction 127.

It is conceivable that the measurement station 119 according to FIG. 3 may not comprise the laser device 135 and/or the backscatter detector 151 and/or may only comprise one of the injector devices 121, 129. It is further conceivable that one, a plurality or all of the measurement stations 23*b* to 23*j*, 25*b* to 25*j* and 27*b* to 27*j* are formed according to the alternative preferred embodiment shown in FIG. 3.

According to a preferred embodiment of the present invention the molecular structure determination facility 1 can be used as follows. The source 3 of a pulsed electron beam 5 emits an electron pulse 157 of a pulsed electron beam 5. The electron pulse 103 enters the switching magnet 9 through the input connection 7. The switching magnet 9 diverts the electron pulse 157 to one of the ten measurement lines 13*a* to 13*j*. The electron pulse 157 leaves the magnet through that one of the ten output connections 11*a* to 11*j* that is connected with the input 21*a* to 21*j* of the X-ray source 15*a* to 15*j* of the one measurement line 13*a* to 13*j*.

When the electron beam 119 enters the X-ray source 15*a* to 15*j* it emits a coherent X-ray pulse 159*a* to 159*j* of the pulsed coherent X-ray beam 17*a* to 17*j* along the emission direction 19*a* to 19*j*. The coherent X-ray pulse 159*a* to 159*j* travels through the measurement stations 23*a* to 23*j*, 25*a* to 25*j*, 27*a* to 27*j* that are aligned along the emission direction 19*a* to 19*j* before it interacts with the X-ray beam analysing device 29*a* to 29*j*. The focusing of the X-ray beam by the focusing units 63, 65, 67 comprised in the measurement stations 23*a* to 23*j* or the position of the emission direction 19*a* to 19*j* relative to the sample beams of liquid 45, 47, 49 can be monitored by the X-ray beam analysing devices 29*a* to 29*j*.

Upon entering a measurement station 23*a* to 23*j*, 25*a* to 25*j*, 27*a* to 27*j* the coherent X-ray pulse 159*a* to 159*j* is focused in the focal spot 69, 71, 73 located in said interaction region 51, 53, 55 using the focusing unit 63, 65, 67. Within each measurement station 23*a* to 23*j*, 25*a* to 25*j*, 27*a* to 27*j* the provided injector device 39, 41, 43 is triggered to inject a sample beam of liquid 45, 47, 49 into the interaction regions 51, 53, 55 such that the coherent X-ray pulse 159*a* to 159*j* intersects the sample beam of liquid 45, 47, 49 in said interaction region 51, 53, 55. Said sample beam of liquid 45, 47, 49 may, for example, be injected at the same rate as the coherent X-ray pulses 159*a* to 159*j* arrive at the measurement station 23*a* to 23*j*, 25*a* to 25*j*, 27*a* to 27*j*. Thereby, the consumption of the sample suspension is reduced, since less material will be flowing overall, yet the material will be flowing during the time that X-ray pulses 159*a* to 159*j* intersect the interaction region 51, 53, 55. This embodiment is especially advantageous when the sample suspension can only be obtained in limited volumes. X-rays 81, 83, 85 emerging the interaction region 51, 53, 55 after the coherent X-ray pulse 159*a* to 159*j* has intersected the sample beam of liquid 45, 47, 49 are detected using the detector 75, 77, 79.

Once the coherent X-ray pulse 159*a* to 159*j* has passed the interaction region 51, 53, 55 it leaves the measurement station 23*a* to 23*j*, 25*a* to 25*j*, 27*a* to 27*j* through the central opening 87, 89, 91 in the detector 75, 77, 79.

In a further preferred embodiment the switching magnet 9 diverts the electron pulse 157 to another one of the ten measurement lines 13*a* to 13*j*. The electron pulse 157 leaves the magnet through that one of the ten output connections 11*a* to 11*j* that is connected with the input 21*a* to 21*j* of the X-ray source 15*a* to 15*j* of the other measurement line 13*a* to 13*j*.

According to another preferred embodiment of the present invention the source 3 emits electron beam pulses 119 at a given repetition rate. Said switching magnet diverts each electron pulse 157 in succession to one of said measurement lines 13*a* to 13*j* such that each X-ray sources 15*a* to 15*j* emits X-ray pulses 159*a* to 159*j* at a repetition rate equal to the repetition rate of the source 3 reduced by a factor equal to the inverse of the number of measurement lines 13*a* to 13*j*. Therefore, the maximum required read-out frequency of the detectors 75, 77, 79 and the maximum required repetition rate of the sample injector devices 39, 41, 43 only has to be equal to the repetition rate of the source 3 reduced by a factor equal to the inverse of the number of measurement lines 13*a* to 13*j* and not equal to the repetition rate of the source 3. Likewise, the rate at which the sample beam of liquid 45, 47, 49 interacts with the coherent X-ray beam 17*a* to 17*j* and those X-rays 81,

83, 85 created in said interaction are detected by the detectors 75, 77, 79 can be increased by a factor equal to the number of measurement lines compared to another preferred embodiment in which the electron pulse 5 is only diverted to one measurement line 13a to 13j.

A molecular structure determination facility 1 according to the above exemplary embodiment has a significantly higher throughput than conventional X-ray crystallography experiments. In an exemplary embodiment a molecular structure determination facility 1 comprises ten measurement lines 13a to 13j each comprising two measurement stations 23a to 23j, 25a to 25j, 27a to 27j. The source 3 emits electron pulses 119 at a frequency of 10 kHz that are evenly distributed among the measurement lines 13a to 13j using the switching magnet 9. Hence, every X-ray source 15a to 15j emits coherent X-ray pulses 159a to 159j at a repetition frequency of 1 kHz. This corresponds to the readout frequency of the detectors.

For each macromolecule diffraction patterns from more than 10,000 crystals have to be measured and summed up. Approximately 10% of the X-ray pulses 159a to 159j hit a nanocrystal. Out of the recorded diffraction patterns roughly half can be indexed successfully. Therefore at total of 200,000 X-ray pulses 159a to 159j is required to obtain sufficient data to fully reconstruct a macromolecule. A particular measurement station 23a to 23j, 25a to 25j, 27a to 27j can therefore measure sufficient diffraction patterns in 200s.

If between two types of suspension that are used as sample beams of liquid 45, 47, 49 the sample injection devices 39, 41, 43 are flushed with a cleaning suspension for 3 minutes the molecular structure determination facility 1 would achieve an output of 200 samples per hour. If the molecular structure determination facility 1 runs with a downtime of 50% a total of 2,400 molecules can be analysed per day. Within one month approximately 70,000 different samples could be studied which compares to the total number of structures that have been publicly released within the last forty years.

In another exemplary embodiment of the present invention a molecular structure determination facility 1 comprising a measurement station 119 with two sample injector devices 121, 129 as described before with reference to FIG. 3 can be used as follows, where only those steps are described that differ from those stated above.

Within a measurement station 119 the injector device 121 and the second injector device 129 are triggered to simultaneously inject a sample beam of liquid 123 and a second sample beam of liquid 131 into the interaction region 125 where the sample beams of liquid 123, 131 mix and a reaction is initiated. The sample beams of liquid 123, 131 are injected such that the coherent X-ray pulse 161 intersects the sample beam of liquid 123 mixed with the second sample beam of liquid 131 in said interaction region 125. X-rays 127 emerging the interaction region 125 after the X-ray pulse 161 has intersected the sample beams of liquid 123, 131 are detected using the detector 145. In such a way the molecular structure determination facility 1 according to the present invention may be used to monitor the change of the shape of a biological macromolecule undergoing a reaction with another biological macromolecule. If diffraction patterns are obtained at different points in time after the mixing of the sample beams of liquid 123, 131 a molecular structure determination facility 1 of the preferred embodiment could be used to study the structural changes of the macromolecules in a time-resolved fashion.

A molecular structure determination facility 1 comprising a measurement station 119 with a laser device 135 could be used in the following exemplary fashion where only those steps are described that differ from the above description.

Upon injection of the sample beams of liquid 123, 131 the laser device 135 may be triggered to emit a laser beam 137 that intersects the sample beams of liquid 123, 131 in the interaction region 125. Said laser device may be, for example, emitting a visible or an infrared light. Thereby, the laser beam 137 may drive the macromolecules comprised in said sample beams of liquid 123, 131 into a photo reaction. The change of the structure of the macromolecule due to the photo reaction can then be studied in the refraction patterns detected by the detectors 145. If diffraction patterns are obtained at different points in time after the initiation of the photo reaction a molecular structure determination facility 1 of the preferred embodiment could be used to study the structural changes of the macromolecules in a time-resolved fashion.

In another exemplary embodiment of the present invention a molecular structure determination facility 1 comprising a measurement station 119 with a backscatter detector 151 as described before with reference to FIG. 3 could be used in the following exemplary fashion where only those steps are described that differ from the above description. After the coherent X-ray pulse 161 has been focused in the focal spot 143 located in said interaction region 125 using the focusing unit 139 it passes through the central opening 155 of the backscatter detector 151. Additional X-rays 153 emerging the interaction region 125 after the X-ray pulse 161 has intersected the sample beam of liquid 131, 137 are detected using the backscatter detector 151. A combination of the diffraction patterns detected by the detector 145 and the backscatter detector 151 allows reconstructing the structure of the molecules with a resolution of up to half the wavelength of the X-ray pulse 161.

What is claimed is:

1. A molecular structure determination facility comprising:
    a first X-ray source capable of emitting a pulsed coherent X-ray beam along a first emission axis;
    a first measurement station aligned along the first emission axis, said first measurement station comprising a first sample injector device, a first focusing unit and a first detector, the first sample injector being configured to inject a first sample beam of liquid into a first interaction region located on said first emission axis, the first interaction region being spaced apart from the first X-ray source by a first distance, the first focusing unit being configured to focus the X-ray beam along the first emission axis in a first focal spot located in said first interaction region and, the first detector being sensitive to X-rays emerging from said first interaction region, said first detector being arranged around said first emission axis and on that side of said first interaction region facing away from said first X-ray source, wherein said first detector comprises a first central opening aligned with said first emission axis; and
    a second measurement station aligned along the first emission axis, said second measurement station comprising a second sample injector device, a second focusing unit and a second detector, the second sample injector being configured to inject a second sample beam of liquid into a second interaction region located on said first emission axis, the second interaction region being spaced apart from the first X-ray source by a second distance that is greater than the first distance, the second focusing unit being configured to focus the X-ray beam along the first emission axis in a second focal spot located in said second interaction region and, the second detector being sensitive to X-rays emerging from said second interaction region, said second detector being arranged around said first emission axis and on that side of said second interaction region facing away from said first X-ray source, wherein said second detector comprises a second central opening aligned with said first emission axis.

2. The molecular structure determination facility of claim 1, wherein a first X-ray beam analysing device is located on said first emission axis on that side of said first and second measurement stations facing away from said first X-ray source.

3. The molecular structure determination facility of claim 2, further comprising:
   a second X-ray source that is that is capable of emitting a second pulsed coherent X-ray beam along a second emission axis,
   a plurality of third measurement stations aligned consecutively along said second emission axis,
   wherein each of said third measurement stations comprises:
      a third sample injector device for injecting a third sample beam of a liquid into a third interaction region located on said second emission axis,
      a third focusing unit that is adapted for focusing the second pulsed coherent X-ray beam in a third focal spot located in said third interaction region,
      a third detector that is sensitive to X-rays emerging from said third interaction region, said third detector being arranged around said second emission axis and on that side of said third interaction region facing away from said second X-ray source, wherein said third detector comprises a third central opening aligned with said second emission axis.

4. The molecular structure determination facility of claim 3, wherein a second X-ray beam analysing device is located on said second emission axis on that side of said third measurement stations facing away from said second X-ray source.

5. The molecular structure determination facility of claim 4, further comprising a pulsed electron beam source that is configured for supplying a pulsed electron beam to said first and second X-ray sources, wherein a switching magnet is provided having an input connection and first and second output connections, said switching magnet being adapted for diverting the pulsed electron beam to either of said first and second output connections,
   wherein said input connection is connected with said pulsed electron beam source,
   wherein said first output connection is connected with said first X-ray source, and
   wherein said second output connection is connected with said second X-ray source.

6. The molecular structure determination facility of claim 5, wherein said first, second and third sample injector devices are connected to a central sample preparation unit comprising:
   a reservoir system including a plurality of reservoirs;
   a plurality of pumps wherein each of said reservoirs is connected with an input of one of said pumps; and
   a switching unit having a plurality of switching unit inputs and a plurality of switching unit outputs,
   wherein the output of each of said pumps is connected with an associated one of said switching unit inputs, and
   wherein each of said switching unit outputs is connected with an associated one of said first, second and third sample injector devices.

7. The molecular structure determination facility of claim 6, wherein one or more of said first, second and third measurement stations comprises a fourth sample injector device for injecting a fourth sample beam of liquid into an associated one of said first, second and third interaction regions.

8. The molecular structure determination facility of claim 7, wherein one or more of said first, second and third measurement stations further comprise a laser device that is configured to emit a laser beam that intersects a corresponding one of said first, second and third interaction regions.

9. The molecular structure determination facility of claim 6, wherein one or more of said first, second and third measurement stations further comprises a backscatter detector that is sensitive to X-rays emerging from at least one of said first, second and third interaction regions, said backscatter detector being arranged around a corresponding one of said first and second emission axes and on that side of said at least one of said first, second and third interaction regions facing away from a corresponding one of said first, second and third detectors,
   wherein said backscatter detector comprises a central backscatter opening aligned with said corresponding one of said first and second emission axes.

10. A molecular structure determination method using the molecular structure determination facility of claim 1, the method comprising:
    emitting a coherent X-ray beam pulse along said first emission axis from said first X-ray source;
    triggering said first and second sample injector devices provided in said first and second measurement stations to inject first and second sample beams of liquid into said first and second interaction regions, respectively, the first and second interaction regions being aligned along said first emission axis such that said coherent X-ray beam pulse intersects said first and second sample beams of liquid in said first and second interaction regions, respectively; and
    detecting X-rays emerging from said first and second interaction regions with said first and second detectors.

11. A molecular structure determination method using the molecular structure determination facility of claim 8, the method comprising:
    emitting a coherent X-ray beam pulse along said second emission axis from said second X-ray source;
    triggering said fourth sample injector devices comprised in said one or more of said third measurement stations to inject one or more fourth sample beams of liquid into corresponding ones of said third interaction regions aligned along said second emission axis such that said coherent X-ray beam pulse intersects said third and fourth sample beams of liquid in said third interaction regions; and
    detecting X-rays emerging from said third interaction regions said third detectors comprised in said third measurement stations.

12. The molecular structure determination method of claim 11, wherein triggering said third sample injector devices to inject the third sample beams of liquid into said third interaction regions further comprises triggering said fourth sample injector devices to inject said fourth sample beams of liquid into said third interaction regions such that said third sample beams of liquid and said fourth sample beams of liquid mix in said third interaction regions to form a mixed sample that is intersected by said coherent X-ray beam pulse.

13. The molecular structure determination method of claim 12, wherein triggering said third sample injector device to inject the third sample beam of liquid into said third interaction region further comprises triggering said laser device to emit the laser beam, such that said laser beam intersects said third sample beam of liquid in said third interaction region comprised in said third measurement station.

14. The molecular structure determination method of claim 12, wherein triggering said third sample injector device to inject the third sample beam of liquid into said third interaction region further comprises triggering said laser device to emit the laser beam, such that said laser beam intersects said sample beam of liquid mixed with said fourth sample beam of liquid in said third interaction region comprised in said third measurement station.

15. The molecular structure determination facility of claim 1, wherein a second X-ray source is provided for emitting a second pulsed coherent X-ray beam along a second emission axis,
    wherein a plurality of third measurement stations are provided aligned consecutively along said second emission axis,
    wherein each of said third measurement stations comprises:
        a third sample injector device for injecting a third sample beam of a liquid into a third interaction region located on said second emission axis,
        a third focusing unit adapted for focusing the second X-ray beam in a third focal spot located in a third interaction region and
        a third detector being sensitive to X-rays emerging from said third interaction region, said third detector being arranged around said second emission axis and on that side of said third interaction region facing away from said second X-ray source
    wherein said third detector comprises a third central opening aligned with said second emission axis.

16. The molecular structure determination facility of claim 1, wherein said first and second sample injector devices are connected to a central sample preparation unit comprising:
    a reservoir system including a plurality of reservoirs;
    a plurality of pumps wherein each of said reservoirs is connected with an input of one of said pumps; and
    a switching unit having a plurality of inputs and a plurality of outputs,
    wherein the output of each of said pumps is connected with an input of said switching unit, and
    wherein said outputs of the switching unit are connected with the first and second sample injector devices.

17. The molecular structure determination facility of claim 16, wherein at least one of said first and second measurement stations comprises a third sample injector device, each of said third sample injector devices being configured to inject a third sample beam of liquid into an associated one of said first and second interaction regions.

18. The molecular structure determination facility of claim 17, wherein at least one of said first and second measurement stations further comprises a laser device that is configured to emit a laser beam, and wherein the laser beam emitted by each of said laser devices is configured to intersect an associated one of said first and second interaction regions.

19. The molecular structure determination facility of claim 16, wherein one or more of said first and second measurement stations further comprises a backscatter detector, wherein each of said backscatter detectors is sensitive to X-rays emerging from an associated one said first and second interaction regions, wherein each of said backscatter detectors is arranged around said first emission axis on that side of said interaction region facing away from said detector, and wherein each of said backscatter detectors has a backscatter opening aligned with said first emission axis.

20. A molecular structure determination method using the molecular structure determination facility of claim 16, the method comprising:
    emitting a coherent X-ray beam pulse along said first emission axis using said first X-ray source;
    triggering said first and second sample injector devices provided in said first and second measurement stations to inject sample beams of liquid into said first and second interaction regions aligned along said first emission axis such that said coherent X-ray beam pulse intersects said sample beams of liquid in said first and second interaction regions aligned along said first emission axis; and
    detecting X-rays emerging from said first and second interaction regions using said first and second detectors provided in said first and second measurement stations.

21. The molecular structure determination method of claim 10, the method comprising triggering a third sample injector device comprised in said first measurement station to inject a third sample beam of liquid into said first interaction region aligned along said first emission axis such that said coherent X-ray beam pulse intersects said first and third sample beams of liquid in said first interaction region.

22. The molecular structure determination method of claim 21, wherein said first and third sample beams of liquid combine to form a mixture and wherein said coherent X-ray beam pulse intersects said mixture in said first interaction region.

23. The molecular structure determination method of claim 21, wherein triggering said third sample injector device to inject the third sample beam of liquid into said first interaction region further comprises triggering a laser device to emit a laser beam, such that said laser beam intersects said third sample beam of liquid in said first interaction region comprised in said first measurement station.

24. The molecular structure determination method of claim 23, wherein said first and third sample beams of liquid combine to form a mixture and wherein said laser beam intersects said mixture in said first interaction region.

25. The molecular structure determination method of claim 10, wherein triggering said first sample injector device to inject the first sample beam of liquid into said first interaction region further comprises triggering a laser device to emit a laser beam, such that said laser beam intersects said first sample beam of liquid in said first interaction region comprised in said first measurement station.

\* \* \* \* \*